US012575712B2

(12) United States Patent
Chung et al.

(10) Patent No.: US 12,575,712 B2
(45) Date of Patent: Mar. 17, 2026

(54) ARTIFICIAL INTELLIGENCE-BASED ENDOSCOPIC DIAGNOSIS AID SYSTEM AND METHOD FOR CONTROLLING SAME

(71) Applicant: CAIMI CO., LTD., Incheon (KR)

(72) Inventors: Jun-Won Chung, Seoul (KR); Kwang-Gi Kim, Incheon (KR)

(73) Assignee: CAIMI CO., LTD., Incheon (KR)

( * ) Notice: Subject to any disclaimer, the term of this patent is extended or adjusted under 35 U.S.C. 154(b) by 0 days.

(21) Appl. No.: 18/646,272

(22) Filed: Apr. 25, 2024

(65) Prior Publication Data

US 2024/0268627 A1      Aug. 15, 2024

Related U.S. Application Data

(63) Continuation      of      application      No. PCT/KR2022/016127, filed on Oct. 21, 2022.

(30) Foreign Application Priority Data

Oct. 26, 2021      (KR) ........................ 10-2021-0143222

(51) Int. Cl.
    *A61B 1/00* (2006.01)
    *A61B 1/273* (2006.01)
(52) U.S. Cl.
    CPC .... *A61B 1/000096* (2022.02); *A61B 1/00006*
          (2013.01); *A61B 1/000094* (2022.02);
                (Continued)
(58) Field of Classification Search
    CPC ............ A61B 1/000096; G06T 7/0012; G06T
                    2207/10068; G06T 2207/20084
    See application file for complete search history.

(56) References Cited

U.S. PATENT DOCUMENTS 11,100,633 B2 *   8/2021   Ngo Dinh ............. G06T 11/203
2016/0022125 A1   1/2016   Nicolau et al.
                        (Continued)

FOREIGN PATENT DOCUMENTS

JP          2013-150650 A      8/2013
KR          10-1599129 B1      3/2016
                (Continued)

OTHER PUBLICATIONS

"Development of a real-time endoscopic image diagnosis support system using deep learning technology in colonoscopy" by M. Yamada et al. Scientific Reports. 14465. 2019.*
                (Continued)

*Primary Examiner* — Jason M Ip
(74) *Attorney, Agent, or Firm* — Bridgeway IP Law Group, PLLC; Jihun Kim

(57)                ABSTRACT
An AI-based endoscopic diagnostic aid system includes: an endoscope module providing an endoscopic image of internal organs of the body of a patient; an input module configured to be capable of inputting arbitrary medical information about the patient; a control module which analyzes the endoscopic image provided from the endoscope module through a pre-stored image processing program to detect lesion information, matches the detected lesion information with the medical information input from the input module through a pre-stored lesion diagnosis program while generating at least one diagnosis information of malignancy and malignancy probability corresponding to the matching result, and outputs a preset notification signal according to the lesion information and the diagnosis information; and a notification module which visually displays on an arbitrary screen according to the notification signal output from the control module.

11 Claims, 7 Drawing Sheets

(52) U.S. Cl.
CPC ...... *A61B 1/000095* (2022.02); *A61B 1/0005*
(2013.01); *A61B 1/273* (2013.01)

(56) References Cited

U.S. PATENT DOCUMENTS

| | | | |
|---|---|---|---|
| 2018/0247107 A1* | 8/2018 | Murthy | G06V 20/698 |
| 2023/0089026 A1* | 3/2023 | Tran | A61B 6/48 |
| | | | 705/2 |

FOREIGN PATENT DOCUMENTS

| | | |
|---|---|---|
| KR | 10-1626802 B1 | 6/2016 |
| KR | 10-2020-0038120 A | 4/2020 |
| KR | 10-2222547 B1 | 3/2021 |
| KR | 10-2237441 B1 | 4/2021 |

OTHER PUBLICATIONS

"Review on the Applications of Deep Learning in the Analysis of Gastrointestinal Endoscopy Images" by W. Du et al. IEEE Access. 2019.*
'Overview of Deep Learning in Gastrointestinal Endoscopy' by J.K. Min. Gut and Liver. vol. 13, No. 4, Jul. 2019, pp. 388-393. (Year: 2019).*

* cited by examiner

S510

START

BLUR IMAGE REMOVAL STEP ~ S511

REPRESENTATIVE IMAGE SELECTION STEP ~ S512

DUPLICATE IMAGE FILTERING STEP ~ S513

END

ARTIFICIAL INTELLIGENCE-BASED ENDOSCOPIC DIAGNOSIS AID SYSTEM AND METHOD FOR CONTROLLING SAME

CROSS-REFERENCE TO RELATED APPLICATIONS

This application is a continuation application of PCT International Application No. PCT/KR2022/016127 filed on Oct. 21, 2022, and claims priority to Korean Patent Application No. 10-2021-0143222 filed on Oct. 26, 2021, the entire disclosures of which are incorporated herein by reference.

TECHNICAL FIELD

The present invention relates to a system that assists an endoscopy diagnosis based on artificial intelligence and a method for controlling the same which automatically detect lesions in real time by using pre-learned endoscopic image data, and apply medical information data including lifestyle habits and environmental factors of a patient undergoing an endoscopic procedure to an artificial intelligence algorithm to improve malignancy degree diagnosis accuracy and efficiency of the lesions.

BACKGROUND ART

Recently, the number of patients diagnosed with stomach cancer tends to continuously increase, and especially in modern times, the number of stomach cancer patients in younger age groups is rapidly increasing.

The causes of such stomach cancer include chronic atrophic gastritis, intestinal dysplasia, gastroenterological anastomosis, dietary factors, Helicobacter pylori infection, genetic factors, and other environmental factors, and the stomach cancer occurs twice as often in men than in women, and occurs more frequently in people in their 50s or 60s.

In addition, although drinking and smoking have not been clearly identified as direct causes of stomach cancer, environmental factors such as lifestyle habits are also emerging as one of the factors causing stomach cancer.

Currently, a specialist is performing the above-described endoscopic procedure for the above-mentioned stomach cancer patients, and lesion diagnosis is being performed by referring to the images provided as a result of the endoscopic procedure.

However, in general, endoscopic procedures are performed 1:1, are labor-intensive and time-consuming, are repetitive, and have inter- and intra-observer variability due to various factors (experience, condition, fatigue, mistakes).

In addition, in conventional endoscopic procedures, images input in real time are processed independently for each image, so for patients with lesions, lesions can be detected in hundreds to thousands of images. Thus, a disadvantage is that it is not easy to analyze and confirm the results after the endoscopic procedures based on this vast amount of images.

In particular, there may be problems with not being able to observe Borrmann type 4 with upper gastrointestinal endoscopy or not being able to observe ulcerative lesions in the blind spot.

Therefore, the need for the endoscopic diagnostic assistance system is increasing, which can diagnose the condition of the lesion more efficiently and easily through an artificial intelligence-based image process, and at the same time, achieve a more accurate diagnosis by considering the patient's lifestyle and environmental factors.

DISCLOSURE

Technical Problem

Accordingly, the present invention is contrived to solve the problems, and the present invention has been made in an effort to provide a system that assists an endoscopy diagnosis based on artificial intelligence and a method for controlling the same which automatically detect lesions in real time by using pre-learned endoscopic image data, and apply medical information data including lifestyle habits and environmental factors of a patient undergoing an endoscopic procedure to an artificial intelligence algorithm to improve malignancy degree diagnosis accuracy and efficiency of the lesions.

However, the technical objects to be achieved by the present invention are not limited to the aforementioned technical objects, and other technical objects, which are not mentioned above, will be apparently appreciated by a person having ordinary skill in the art from the following description.

Technical Solution

According to an exemplary embodiment of the present invention, a system that assists an endoscopy diagnosis based on artificial intelligence, which is a technical means for achieving the objects may include: an endoscope module providing an endoscopic image for body's internal organs of a patient; an input module configured to input arbitrary medical information about the patient; a control module analyzing the endoscopic image provided from the endoscope module through a pre-stored image processing program to detect lesion information, and matching the detected lesion information and the medical information input from the input module, and generating at least one diagnosis information of malignancy and a malignancy probability corresponding to the matching result through a pre-stored lesion diagnosis program, and outputting a preset notification signal according to the lesion information and the diagnosis information; and a notification module visually displaying on an arbitrary screen according to the notification signal output from the control module, and the control module may match and classify a plurality of frame images for the endoscopic image with respective regions of the internal organs of the body, respectively through an image processing program to which a deep learning model is applied, further generate search information for distinguishing a search completion region and an unsearched region according to the classification result, and output a preset notification signal according to the generated search information.

Further, the image processing program of the control module may be a deep learning-based program that is pre-learned by first acquiring a plurality of frame images in which lesions appear in a plurality of endoscopic images acquired by pre-capturing body's internal organs of multiple patients, and the lesion diagnosis program of the control module may be a deep learning-based program that is pre-matched and learned by first acquiring the plurality of frame images in which the lesions appear and a plurality of medical information for multiple patients corresponding thereto.

Further, the control module may include: an image acquisition unit acquiring the endoscopic image provided from the endoscope module at a plurality of frames per second; an image conversion unit converting the frame image acquired by the image acquisition unit to meet a condition of the image processing program; a lesion detection unit analyzing the frame image converted by the image conversion unit through the image processing program to detect lesion information including the size, shape, and coordinates of the lesion on the image; a database unit storing a plurality of frame images in which lesions appear in a plurality of endoscopic images acquired by pre-capturing the body's internal organs of multiple patients, and storing a plurality of medical information for multiple patients corresponding to the plurality of frame images in which the lesions appear, and providing a learning environment of the image processing program and a learning environment of the lesion diagnosis program; a lesion diagnosis unit matching the lesion information detected by the lesion detection unit and the medical information input from the input module through the lesion diagnosis program, and generating at least one diagnosis information of the malignancy and the malignancy probability corresponding to the matching result; a search region confirmation unit receiving the frame image converted by the image conversion unit in real time and classifying which region of the body's internal organs the frame image matches into an arbitrary category through the image processing program, determining whether the classified frame image is classified into a category of the same region continuously in 30 frames, and generating search information for distinguishing the search completion region and the unsearched region according to the determination result; and a notification signal output unit outputting a preset notification signal according to the lesion information detected by the lesion detection unit, the diagnosis information generated by the lesion diagnosis unit, and the search information generated by the search region confirmation unit.

Further, the image processing program of the lesion detection unit may be configured to acquire a lesion region on the image by learning 10,000 to 11,000 frame images in which lesions appear in the plurality of endoscopic images acquired by pre-capturing the body's internal organs of the multiple patients, acquire data for the coordinates of the lesion on the image by using weighted bi-directional FPN (BiFPN) in a feature point extracted through an EfficientNetB0 structure while using an EfficientDet structure having EfficientNetB0 as backbone, and acquire data for a size and a shape of the lesion on the image through pixel analysis.

Further, the lesion detection unit may be configured to recognize whether the lesion information is continuously detected in frames images of 10 or more frames among the frame images converted by the image conversion unit, and when the database unit recognizes that the lesion information is continuously detected in frame images of 10 or more frames through the lesion detection unit, the database unit may separately store the frame images, and the lesion diagnosis unit may operate only when recognizing that the lesion detection unit continuously detects the lesion information in the frame images of 10 or more frames.

Further, the lesion diagnosis program of the lesion diagnosis unit may be configured to match and learn 2000 to 2100 frame images in which the lesions appear and 2000 to 2100 medical information for 2000 to 2100 patients corresponding thereto, and diagnose the degree of malignancy for the lesion on the image, and match the data of the medical information with the feature point extracted through the EfficientNetB0 structure, and acquire data for the malignancy and the malignancy probability of the lesion on the image.

Further, the search region confirmation unit may classify the frame images into a total of 10 categories related to the gastrointestinal tract among the internal organs of the body through the EfficientNetB0 structure of the image processing program, and the 10 categories may be esophagus, squamocolumnar junction, middle upper body, lower body, antrum, duodenal bulb, duodenal descending, angulus, retroflex middle upper body, and fundus.

Further, when the search region confirmation unit determines that the classified frame image is classified into the category of the same region continuously in 30 frames, the search region confirmation unit may handle the corresponding region as the search completion region in which the search by the endoscope module is sufficient to generate first search information corresponding thereto, and the notification signal output unit may output a notification signal which may be displayed in at least one form of the snapshot image and the text for the search completion region according to the first search information generated by the search region confirmation unit.

Further, when the search region confirmation unit determines that the classified frame image is not classified into the category of the same region continuously in 30 frames at a time when the procedure using the endoscope module is terminated, the search region confirmation unit may handle the corresponding region as the unsearched region in which the search by the endoscope module is insufficient to generate second search information corresponding thereto, and the notification signal output unit may output a notification signal which may be displayed in at least one form of the snapshot image and the text for the unsearched region according to the second search information generated by the search region confirmation unit.

Further, the notification signal output unit may output a notification signal that is capable of displaying a frame image in which the lesion information is detected on a screen of the notification module in the form of a snapshot image, to be positioned on the snapshot image to correspond to coordinates of a lesion in the lesion information and to have a size corresponding to the size of the lesion, output a notification signal capable of displaying a polygonal solid line corresponding to the shape of the lesion in a mapping form, and output a notification signal which may be displayed in a form of mapping an OX text corresponding to the malignancy in the diagnosis information, and a combination text of a number and a percent (%) corresponding to the malignancy probability in the diagnosis information on the snapshot image.

Further, the control module may further include an image selection unit that recognizes that the lesion information is continuously detected through the image processing program and selects one representative frame image among the frame images of 10 or more frames separately stored in the database unit, and the image selection unit may include: a blur image removal unit removing at least one blur image in which the blur phenomenon appears from the frame images of 10 or more frames separately stored in the database unit, by using the image processing program; a representative image selection unit selecting a plurality of representative images from an image list from which the blur image is removed through the blur image removal unit; and a duplicate image filtering unit determining whether the same lesion information is detected among the selected representative images, and when determining that the same lesion information is detected, handling the selected representative images as a duplicate image, and filtering the remaining representative images other than one of the selected representative images.

Further, the image processing program of the image selection unit may learn a blur phenomenon based on 2700 to 2800 frame images in which the lesions appear in the plurality of endoscopic images acquired by pre-capturing the body's internal organs of the multiple patients, the blur image removal unit may obtain a blur probability for the frame images of 10 or more frames separately stored in the database unit through the image processing program, and classify whether the frame images are blurred by the EfficientNetB6 structure of the image processing program, and remove a blur image, and the representative image selection unit may handle that the same lesion information is detected in frame images consecutively continued within 15 to 30 frames in the image list from which the blur image is removed through the blur image removal unit, and select a ¼ quantile frame image, a central frame image, and a ¾ quantile frame image among the frame images as the representative image.

Further, the image processing program of the image selection unit may learn detection of the same lesion information based on 6000 to 6100 frame images in which the lesions appear in the plurality of endoscopic images acquired by pre-capturing the body's internal organs of the multiple patients, and the duplicate image filtering unit obtains a probability of detecting the same lesion information among the selected representative images through the image processing program, and compare an inter-vector similarity of vectors acquired in a pre-coupling layer which is a last layer in the EfficientNetB6 structure of the image processing program through an Annoy algorithm, and determine whether the same lesion information is detected.

Meanwhile, a method for controlling a system that assists an endoscopy diagnosis based on artificial intelligence, which is a technical means for achieving the objects may include: a) providing, by an endoscope module, an endoscopic image for body's internal organs of an arbitrary procedure target patient in real time; b) acquiring, by a control module, the endoscopic image provided in step a) above at a plurality of frames per second, and converting the frame image according to the acquisition to meet a condition of the image processing program; c) analyzing, by the control module, the frame image converted in step b) above through the image processing program to detect lesion information; d) recognizing, by the control module, whether the lesion information is continuously detected in frames images of 10 or more frames among the frame images converted in step b) above according to a detection result of step c) above; e) matching, by the control module, the continuously detected lesion information and medical information input from an input module with each other through a lesion diagnosis program, and generating diagnosis information corresponding to the matching result when it is recognized that the lesion information is continuously detected in the frame images of 10 or more frames according to a recognition result of step d) above; and f) outputting, by the control module, a preset notification signal according to the continuously detected lesion information and the diagnosis information generated in step e) above, and visually displaying, by a notification module, on an arbitrary screen according to a notification signal output from the control module, and the method may further include c') matching and classifying, by the control module, the frame images converted in step b) above with respective regions of the internal organs of the body, respectively, and further generating search information for distinguishing a search completion region and an unsearched region according to the classification result, and outputting a preset notification signal according to the generated search information, and then performing a display process of the notification module in step f) above.

Further, in step d) above, the control module may allow step a) above to be first performed again when the lesion information is not detected according to a detection result of step c) above, and in step e) above, the control module may allow step a) above to be first performed again when it is recognized that the lesion information is not continuously detected in the frame images of 10 or more frames according to a recognition result of step d) above.

Further, step c') above may include c'-1) receiving, by the control module, the frame image converted in step b) above in real time and classifying which region of the internal organs of the body the frame image matches into an arbitrary category through the image processing program, c'-2) determining, by the control module, whether the frame image classified in step c'-1) above is classified into a category of the same region continuously in 30 frames, and c'-3) generating, by the control module, search information for distinguishing a search completion region and an unsearched region according to a determination result in step c'-2) above, and outputting a preset notification signal according to the generated search information, and then performing the display process of the notification module in step f) above.

Further, in step c'-3) above, when the control module determines that the classified frame image is classified into the category of the same region continuously in 30 frames according to a determination result of step c'-2) above, the control module may handle the corresponding region as the search completion region in which the search by the endoscope module is sufficient to generate first search information corresponding thereto, when it is determined that the image frame is not classified into the category of the same region continuously in 30 frames at a time when the procedure using the endoscope module is in progress, step a) above may be allowed to be first performed again, and when it is determined that the classified frame image is not classified into the category of the same region continuously in 30 frames at a time when the procedure using the endoscope module is terminated, the corresponding region may be handled as the unsearched region in which the search by the endoscope module is insufficient to generate second search information corresponding thereto.

Further, step e) above may further include e-1) selecting, by the control module, one representative frame image among the frame images of 10 or more frames through the image processing program when recognizing that the lesion information is continuously detected in the frame images of 10 or more frames according to a recognition result of step d) above; and step e-1) above may include e-11) removing, by the control module, at least one blur image in which a blur phenomenon appears for the frame images of 10 or more frames, e-12) selecting, by the control module, a plurality of representative images in an image list from which the blur image is removed through step e-11) above, and e-13) determining, by the control module, whether the same lesion information is detected among the selected representative images, and when determining that the same lesion information is detected, handling the selected representative images as a duplicate image, and filtering the remaining representative images other than one of the selected representative images.

Advantageous Effects

According to the present invention, a system that assists an endoscopy diagnosis based on artificial intelligence and a method for controlling the same has an effect of automatically detecting lesions in real time by using pre-learned endoscopic image data, and applying medical information data including lifestyle habits and environmental factors of a patient undergoing an endoscopic procedure to an artificial intelligence algorithm to improve malignancy degree diagnosis accuracy and efficiency of the lesions.

Further, according to the present invention, there is an advantage of preventing blind spots through a configuration that allows a region of internal organs of the body to be searched by an endoscope module to be confirmed.

However, effects which can be obtained in the present invention are not limited to the aforementioned effects and other unmentioned effects will be clearly understood by those skilled in the art from the following description.

Figure 1:
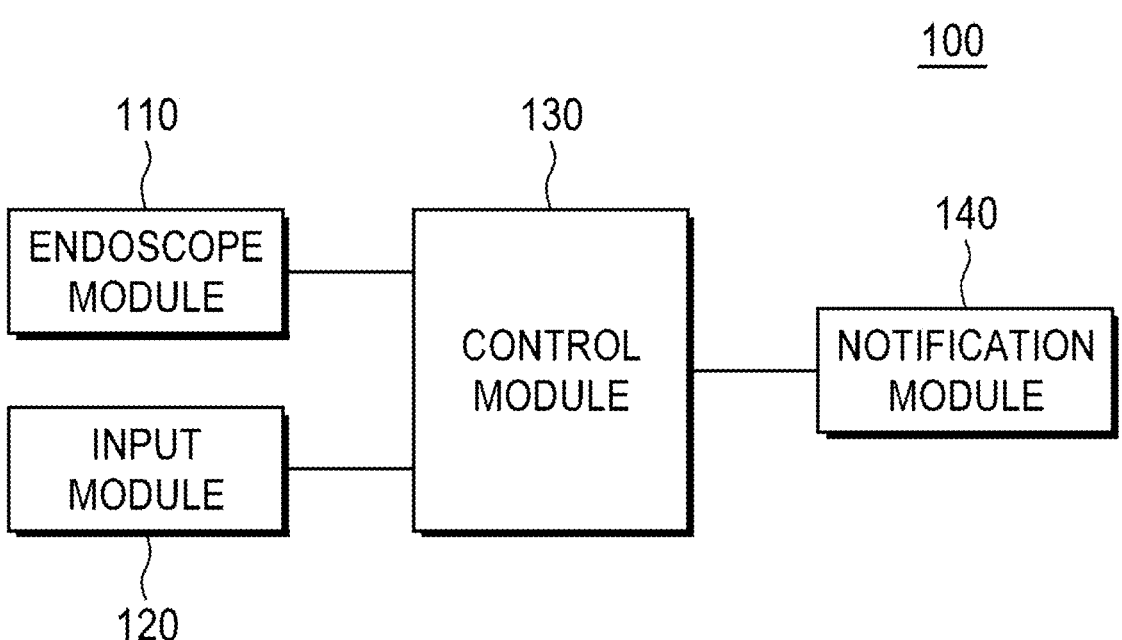
FIG. 1 is a block diagram schematically illustrating an electronic configuration of a system that assists an endoscopy diagnosis based on artificial intelligence according to an exemplary embodiment of the present invention.

DESCRIPTION OF MAIN REFERENCE
NUMERALS OF DRAWINGS

100: Endoscopy diagnosis-assisting system
110: Endoscope module
120: Input module
130: Control module
131: Image acquisition unit
132: Image conversion unit
133: Lesion detection unit
134: Database unit
135: Lesion diagnosis unit
136: Search region confirmation unit
137: Notification signal output unit
138: Image selection unit
138a: Blur image removal unit
138b: Representative image selection unit
138c: Duplicate image filtering unit
140: Notification module

BEST MODE

Hereinafter, exemplary embodiments of the present invention will be described in detail so as to be easily implemented by those skilled in the art, with reference to the accompanying drawings. However, a description of the present invention is merely an exemplary embodiment for a structural or functional description and the scope of the present invention should not be construed as being limited by exemplary embodiments described in a text. That is, since the exemplary embodiment can be variously changed and have various forms, the scope of the present invention should be understood to include equivalents capable of realizing the technical spirit. Further, it should not be understood that since a specific exemplary embodiment does not have to include all objects or effects or include only the effect, the scope of the present invention is limited by the object or effect.

Meanings of terms described in the present invention should be understood as follows.

The terms "first," "second,", and the like are used to differentiate a certain component from other components, but the scope should not be construed to be limited by the terms. For example, a first component may be referred to as a second component, and similarly, the second component may be referred to as the first component. It should be understood that, when it is described that a component is "connected to" another component, the component may be directly connected to another component or a third component may be present therebetween. In contrast, it should be understood that, when it is described that a component is "directly connected to" another component, it is understood that no component is present between the component and another component. Meanwhile, other expressions describing the relationship of the components, that is, expressions such as "between" and "directly between" or "adjacent to" and "directly adjacent to" should be similarly interpreted.

It is to be understood that the singular expression encompasses a plurality of expressions unless the context clearly dictates otherwise and it should be understood that term "include" or "have" indicates that a feature, a number, a step, an operation, a component, a part or the combination thereof described in the specification is present, but does not exclude a possibility of presence or addition of one or more other features, numbers, steps, operations, components, parts or combinations thereof, in advance.

If it is not contrarily defined, all terms used herein have the same meanings as those generally understood by those skilled in the art. Terms which are defined in a generally used dictionary should be interpreted to have the same meaning as the meaning in the context of the related art, and are not interpreted as an ideal meaning or excessively formal meanings unless clearly defined in the present invention.

Figure 2:
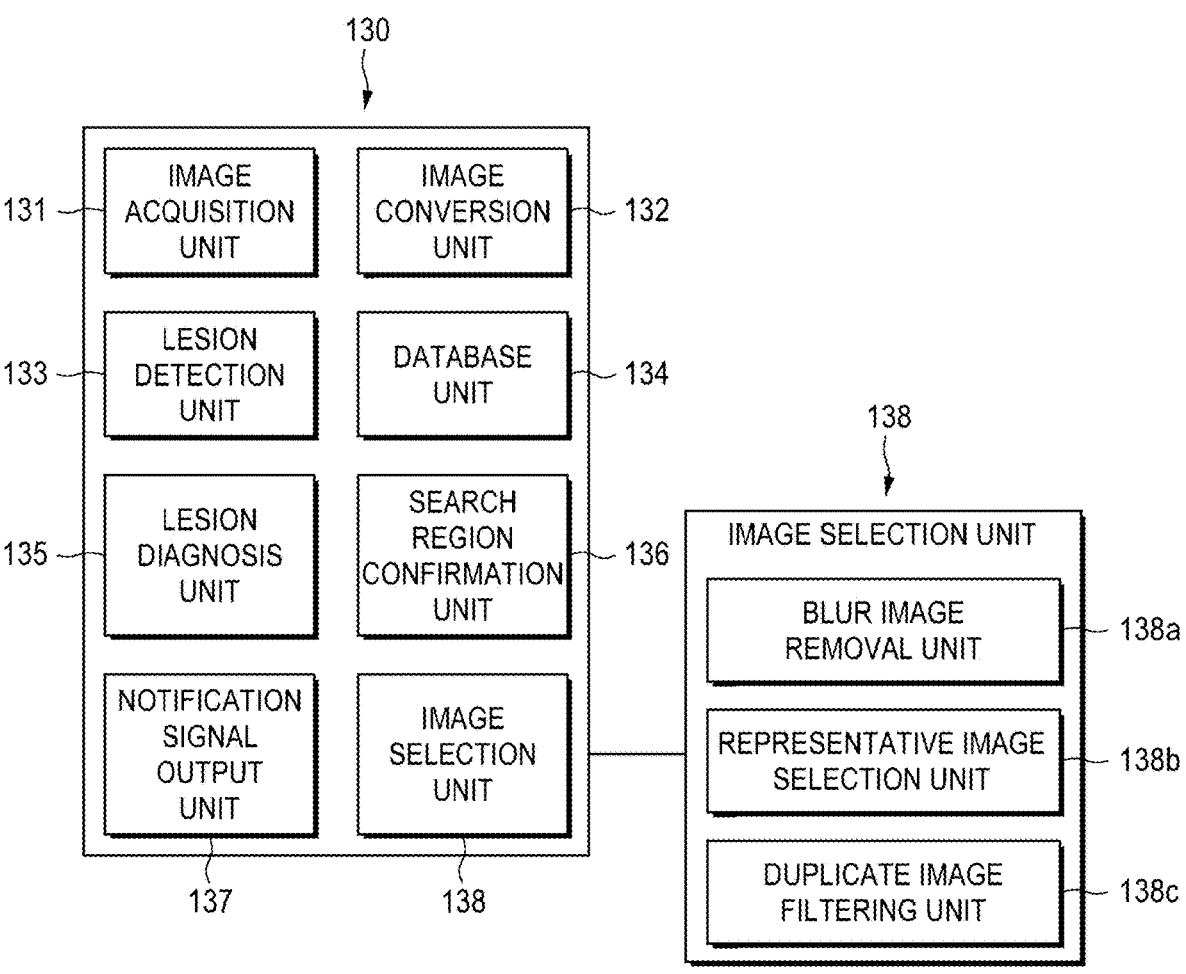
FIG. 2 is a block diagram schematically illustrating an electronic configuration of a control module in the system that assists an endoscopy diagnosis according to FIG. 1.
Figure 3:
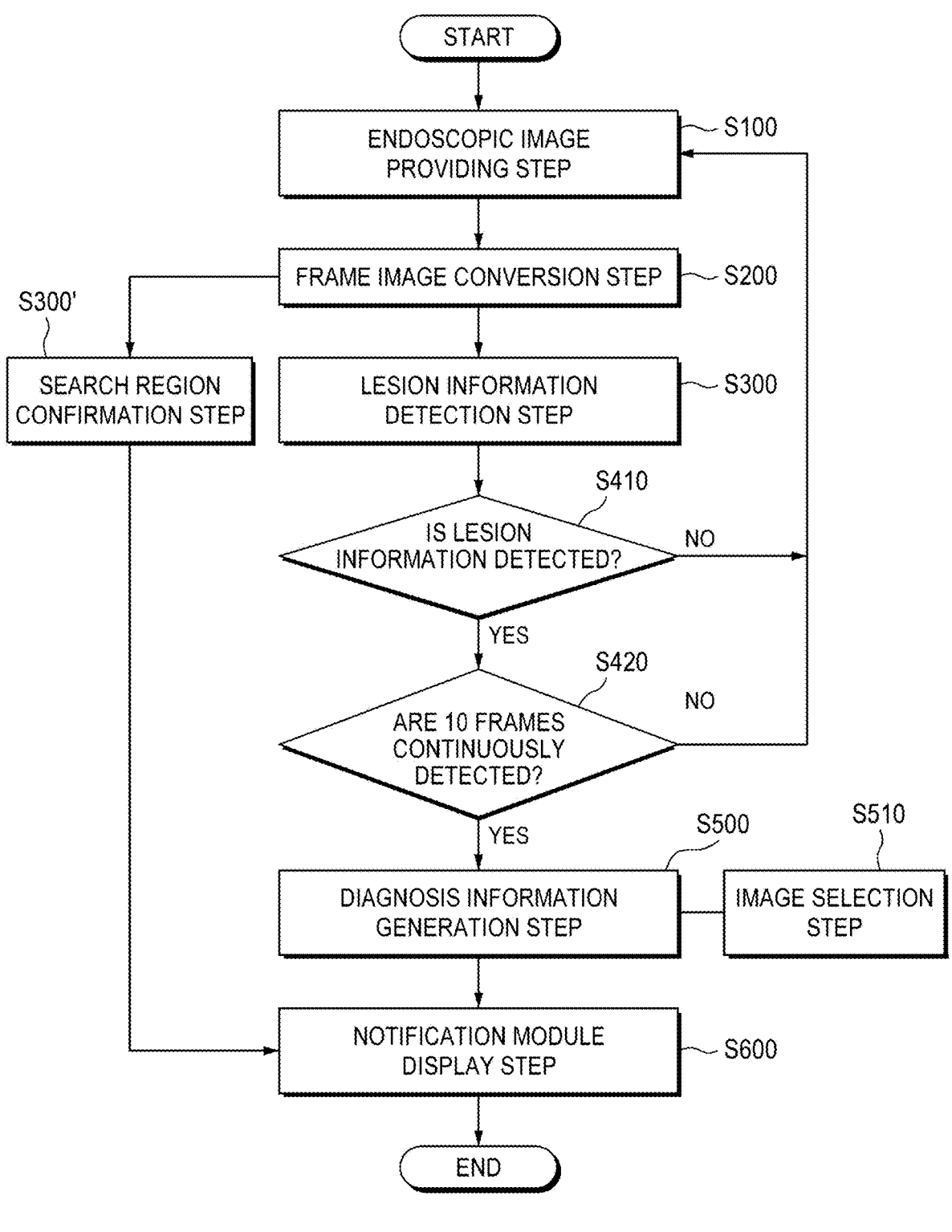
FIG. 3 is a flowchart illustrating a method for controlling a system that assists an endoscopy diagnosis based on artificial intelligence according to an exemplary embodiment of the present invention.
Figure 4:
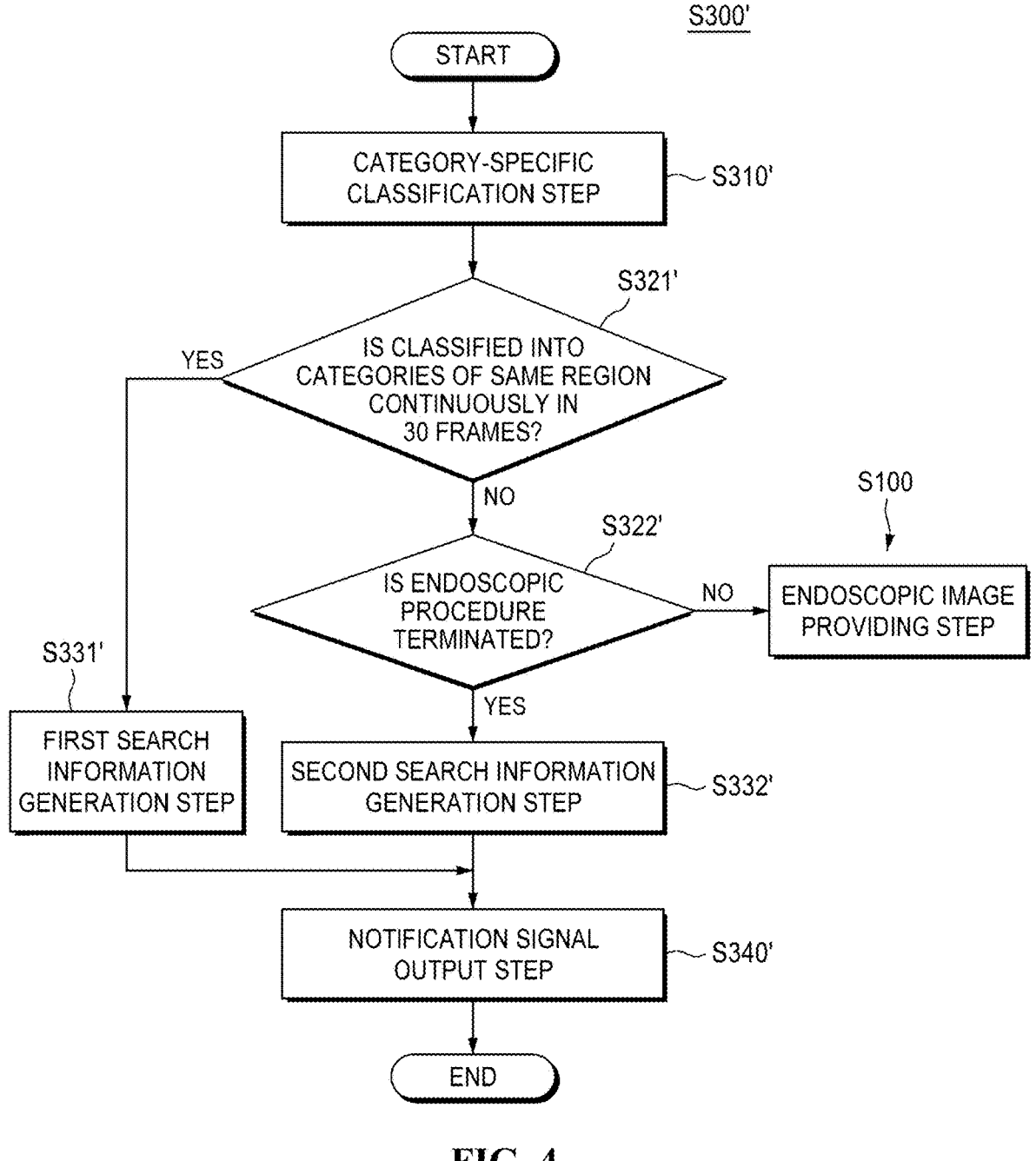
FIG. 4 is a flowchart illustrating a search region confirming step in the method for controlling a system that assists an endoscopy diagnosis according to FIG. 3.
Figure 5:
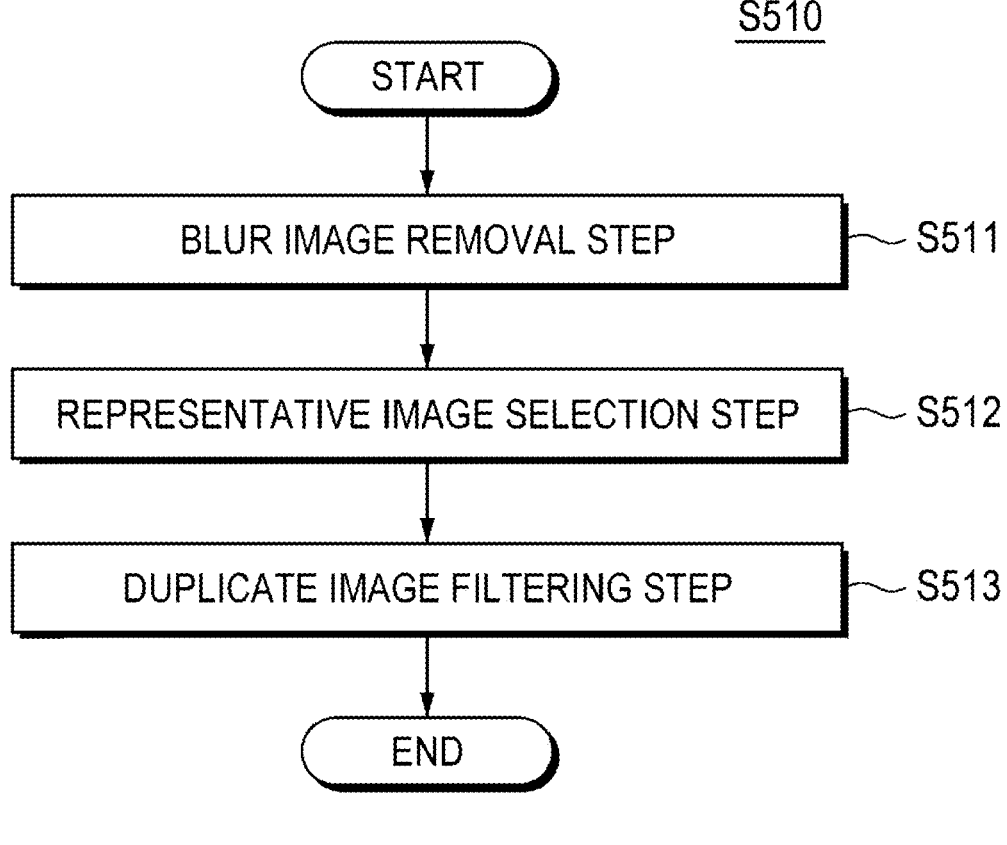
FIG. 5 is a flowchart illustrating an image selecting step in the method for controlling a system that assists an endoscopy diagnosis according to FIG. 3.
Figure 6:
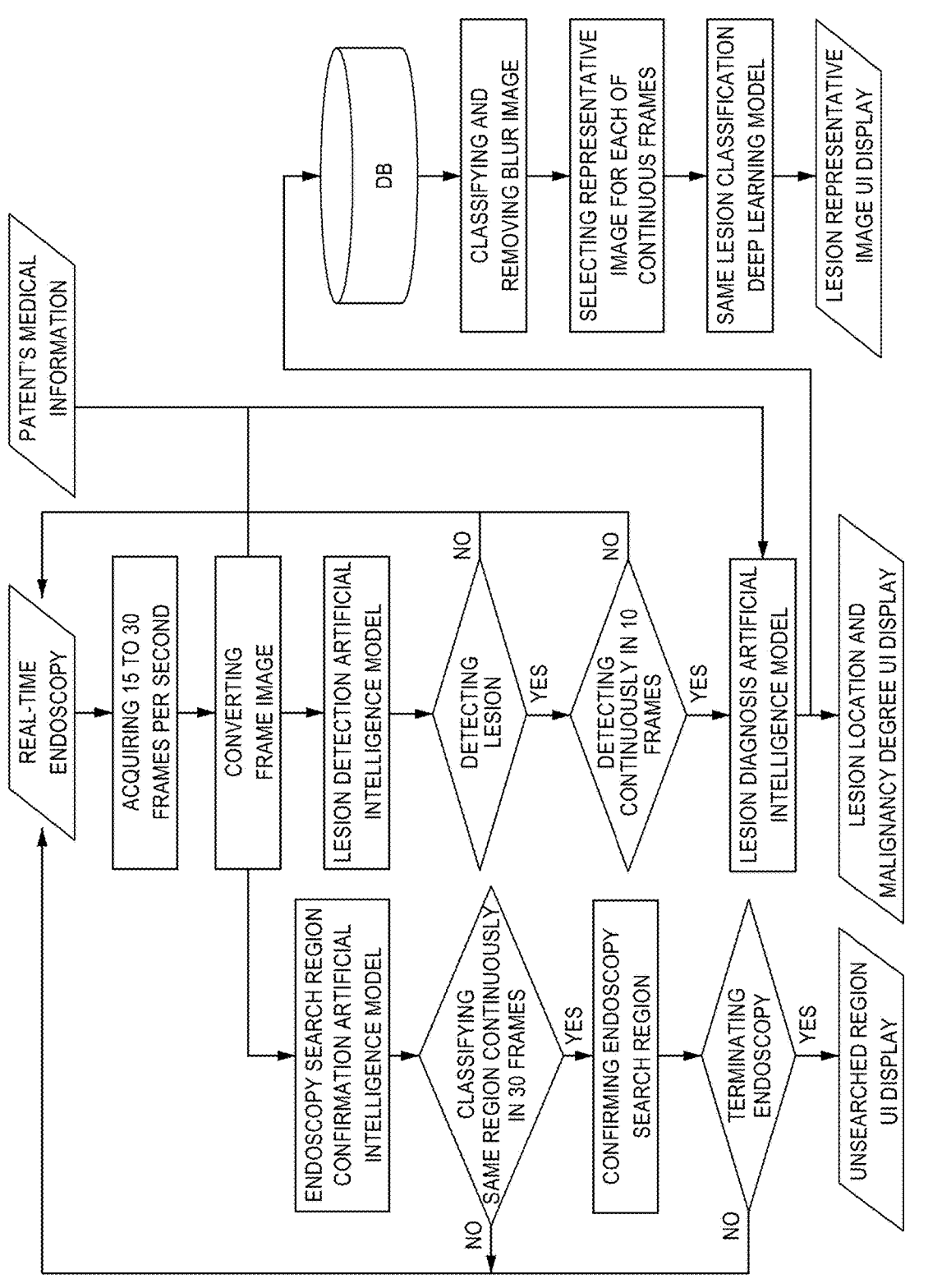
FIG. 6 is a design diagram schematically illustrating an entire process for the system that assists an endoscopy diagnosis based on artificial intelligence and the method for controlling the same according to an exemplary embodiment of the present invention.
Figure 7:
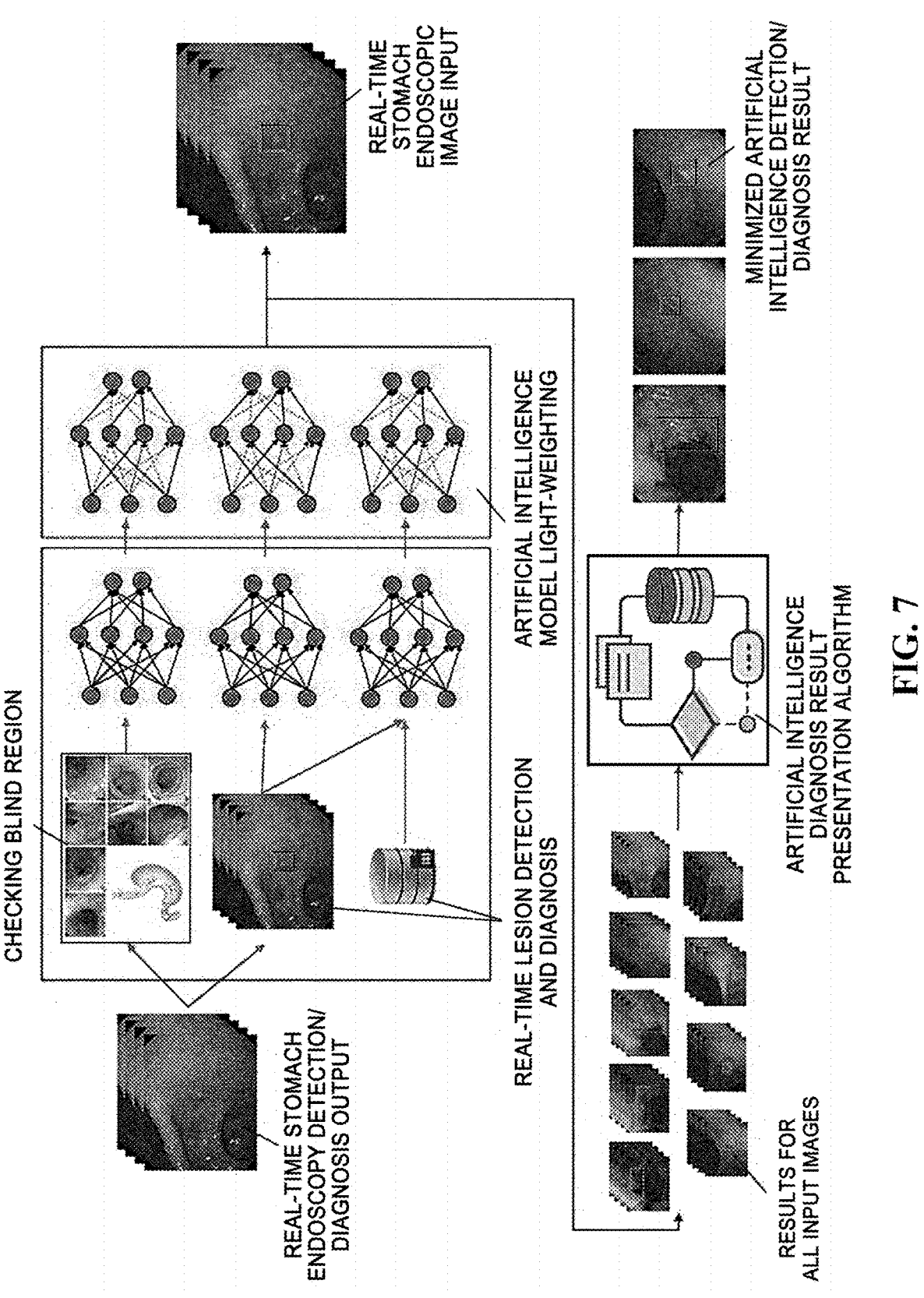
FIG. 7 is a diagram exemplarily illustrating a result to which the process according to FIG. 6 above is applied.

FIG. 1 is a block diagram schematically illustrating an electronic configuration of a system that assists an endoscopy diagnosis based on artificial intelligence according to an exemplary embodiment of the present invention, FIG. 2 is a block diagram schematically illustrating an electronic configuration of a control module in the system that assists an endoscopy diagnosis according to FIG. 1, FIG. 3 is a flowchart illustrating a method for controlling a system that assists an endoscopy diagnosis based on artificial intelligence according to an exemplary embodiment of the present invention, FIG. 4 is a flowchart illustrating a search region confirming step in the method for controlling a system that assists an endoscopy diagnosis according to FIG. 3, FIG. 5 is a flowchart illustrating an image selecting step in the method for controlling a system that assists an endoscopy diagnosis according to FIG. 3, FIG. 6 is a design diagram schematically illustrating an entire process for the system that assists an endoscopy diagnosis based on artificial intelligence and the method for controlling the same according to an exemplary embodiment of the present invention, and FIG. 7 is a diagram exemplarily illustrating a result to which the process according to FIG. 6 above is applied.

As illustrated in FIG. 1, the system 100 that assists an endoscopy diagnosis based on artificial intelligence according to the present invention may be configured to include an endoscope module 110, an input module 120, a control module 130, and a notification module 140.

The endoscope module 110, as a device including an image sensor (not illustrated) provided to be capable of photographing body's internal organs of a patient and a monitor (not illustrated) provided to be capable of displaying an image captured from the image sensor to perform an endoscopic procedure, performs a function of providing an endoscopic image for the internal organs of the body of the patient to the control module 130 to be described later.

Since this endoscope module 110 is a commonly known technical configuration which is generally disclosed, a more detailed description will be omitted, and may be modified and designed in various ways within the technical scope of the present invention by a person skilled in the relevant field.

The input module 120 is provided to provide an input environment to the operator (user), and more specifically, the input module 120 may be configured to input arbitrary medical information about the patient.

Here, the input module 120 preferably adopts a PC keyboard or mouse, but as the input module 120, a keypad of a tablet, smartphone, or the like may also be handled, but is not limited thereto, and of course, a variety of input devices can be handled by those skilled in the art within the technical scope of the present invention.

In addition, according to the present invention, the medical information is preferably personal information for each patient that includes at least one medical-related data among the patient's gender, age, smoking status, drinking status, and underlying disease.

The control module 130 may be configured to analyze the endoscopic image provided from the above-described endoscope module 110 through a pre-stored image processing program to detect lesion information, and match the detected lesion information and the medical information input from the input module 120, and generate at least one diagnosis information of malignancy and a malignancy probability corresponding to the matching result through a pre-stored lesion diagnosis program, and output a preset notification signal according to the lesion information and the diagnosis information.

Meanwhile, according to the present invention, the control module 130 may also be configured to match and classify a plurality of frame images for the endoscopic image with respective regions of the internal organs of the body, respectively through an image processing program to which a deep learning model is applied, further generate search information for distinguishing a search completion region and an unsearched region according to the classification result, and output a preset notification signal according to the generated search information.

Here, the image processing program of the control module 130 is preferably a deep learning-based program that is pre-learned by first acquiring a plurality of frame images in which lesions appear in a plurality of endoscopic images acquired by pre-capturing body's internal organs of multiple patients.

Further, a lesion diagnosis program of the control module 130 is preferably a deep learning-based program that is pre-matched and learned by first acquiring the plurality of frame images in which the lesions appear and a plurality of medical information for multiple patients corresponding thereto.

More specifically, the control module 130 may be configured to include an image acquisition unit 131, an image conversion unit 132, a lesion detection unit 133, a database unit 134, a lesion diagnosis unit 135, and a search region confirmation unit 136, and a notification signal output unit 137, and hereinafter, with reference to FIG. 2, a sub-configuration of the control module 130 will be described in more detail.

The image acquisition unit 131 is preferably configured to acquire the endoscopic image provided from the endoscope module 110 at a plurality of frames per second, and according to a preferred exemplary embodiment of the present invention, the endoscopic image is preferably configured to be acquired at 15 to 30 frames per second.

The image conversion unit 132 is configured to convert the frame image acquired by the image acquisition unit 131 to meet a condition of the image processing program, and more specifically, performs a function of converting 8-bit frame images constituted by pixels of an average specification of 800 width by 1200 height, and having a pixel distribution between 0 and 255 in the related art, to have a pixel distribution between $-1$ and $+1$.

The lesion detection unit 133 may be configured to analyze the frame image converted by the image conversion unit 132 through the image processing program to detect lesion information including the size, shape, and coordinates of the lesion on the image.

At this time, the image processing program of the lesion detection unit 133 acquires a lesion region on the image by learning 10,000 to 11,000 frame images in which lesions appear in a plurality of endoscopic images acquired by pre-capturing the body's internal organs of the multiple patients, acquire data for the coordinates of the lesion on the image by using weighted bi-directional FPN (BiFPN) in a feature point extracted through an EfficientNetB0 structure while using an EfficientDet structure having EfficientNetB0 as backbone, and acquire data for a size and a shape of the lesion on the image through pixel analysis.

In addition, the lesion detection unit 133 may be configured to recognize whether the lesion information is continuously detected in frames images of 10 or more frames among the frame images converted by the image conversion unit 132.

The database unit 134 performs a function of storing a plurality of frame images in which lesions appear in a plurality of endoscopic images acquired by pre-capturing the internal organs of the body of multiple patients, and storing a plurality of medical information for multiple patients corresponding to the plurality of frame images in which the lesions appear, and providing a learning environment of the image processing program and a learning environment of the lesion diagnosis program.

Here, when the database unit 134 recognizes that the lesion information is continuously detected in frame images of 10 or more frames through the lesion detection unit 133, the database unit 134 is preferably configured to separately store the frame images.

The lesion diagnosis unit 135 may be configured to match the lesion information detected by the lesion detection unit 133 and the medical information input from the input module 120 through the lesion diagnosis program, and generate at least one diagnosis information of the malignancy and the malignancy probability corresponding to the matching result.

According to the present invention, the lesion diagnosis unit 135 may operate only when recognizing that the lesion detection unit 133 continuously detects the lesion information in the frame images of 10 or more frames.

At this time, the lesion diagnosis program of the lesion diagnosis unit 135 may be configured to match and learn 2000 to 2100 frame images in which the lesions appear and 2000 to 2100 medical information for 2000 to 2100 patients corresponding thereto, and diagnose the degree of malignancy for the lesion on the image, and match the data of the medical information with the feature point extracted through the EfficientNetB0 structure, and acquire data for the malignancy and the malignancy probability of the lesion on the image.

The search region confirmation unit 136 performs a function of receiving the frame image converted by the image conversion unit 132 in real time and classifying which region of the internal organs of the body the frame image matches into an arbitrary category through the image processing program, determining whether the classified frame image is classified into a category of the same region continuously in 30 frames, and generating search information for distinguishing the search completion region and the unsearched region according to the determination result.

The search region confirmation unit 136 may be configured to classify the frame images into a total of 10 categories related to the gastrointestinal tract among the internal organs of the body through the EfficientNetB0 structure of the image processing program described above.

Here, the 10 categories are preferably esophagus, squamocolumnar junction, middle upper body, lower body, antrum, duodenal bulb, duodenal_descending, angulus, retroflex middle upper body, and fundus.

For example, when the search region confirmation unit 136 determines that the classified frame image is classified into the category of the same region continuously in 30 frames, the corresponding region is handled as the search completion region in which the search by the endoscope module 110 is sufficient to generate first search information corresponding thereto.

Meanwhile, when the search region confirmation unit 136 determines that the classified frame image is not classified into the category of the same region continuously in 30 frames at a time when the procedure using the endoscope module 110 is terminated, the search region confirmation unit 136 handles the corresponding region as the unsearched region in which the search by the endoscope module 110 is insufficient to generate second search information corresponding thereto.

The notification signal output unit 137 performs a function of outputting a preset notification signal according to the lesion information detected by the lesion detection unit 133, the diagnosis information generated by the lesion diagnosis unit 135, and the search information generated by the search region confirmation unit 136.

More specifically, the notification signal output unit 137 may be configured to output a notification signal that is capable of displaying a frame image in which the lesion information is detected on a screen of the notification module 140 to be described later in the form of a snapshot image, to be positioned on the snapshot image to correspond to coordinates of a lesion in the lesion information and to have a size corresponding to the size of the lesion, output a notification signal capable of displaying a polygonal solid line corresponding to the shape of the lesion in a mapping form, and output a notification signal which may be displayed in a form of mapping an OX text corresponding to the malignancy in the diagnosis information, and a combination text of a number and a percent (%) corresponding to the malignancy probability in the diagnosis information on the snapshot image.

In addition, the notification signal output unit 137 may be configured to output a notification signal which may be displayed in at least one form of the snapshot image and the text for the search completion region according to the first search information generated by the search region confirmation unit 136, and configured to output a notification signal which may be displayed in at least one form of the snapshot image and the text for the unsearched region according to the second search information generated by the search region confirmation unit 136.

Meanwhile, the control module 130 may be configured to further include an image selection unit 138 that recognizes that the lesion information is continuously detected through the image processing program and selects one representative frame image among the frame images of 10 or more frames separately stored in the database unit 134.

Here, according to the present invention, the image processing program of the image selection unit 138 is preferably configured to learn a blur phenomenon based on 2700 to 2800 frame images in which the lesions appear in the plurality of endoscopic images acquired by pre-capturing the internal organs of the body of the multiple patients.

Further, the image processing program of the image selection unit 138 is preferably configured to learn detection of the same lesion information based on 6000 to 6100 frame images in which the lesions appear in the plurality of endoscopic images acquired by pre-capturing the internal organs of the body of the multiple patients.

The image selection unit 138 may be configured to include, more specifically, a blur image removal unit 138a, a representative image selection unit 138b, and a duplicate image filtering unit 138c, and hereinafter, a sub-configuration of the image selection unit 138 will be described in more detail as follows.

The blur image removal unit 138a performs a function of removing at least one blur image in which the blur phenomenon appears from the frame images of 10 or more frames separately stored in the database unit 134.

More preferably, the blur image removal unit 138a may obtain a blur probability for the frame images of 10 or more frames separately stored in the database unit 134 through the image processing program, and classify whether the frame images are blurred by the EfficientNetB6 structure of the image processing program, and remove a blur image.

The representative image selection unit 138b performs a function of selecting a plurality of representative images from an image list from which the blur image is removed through the blur image removal unit 138a.

More preferably, the representative image selection unit 138b uses the image processing program to handle that the same lesion information is detected in frame images consecutively continued within 15 to 30 frames in the image list from which the blur image is removed through the blur image removal unit 138a, and select a ¼ quantile frame image, a central frame image, and a ¾ quantile frame image among the frame images as the representative image.

The duplicate image filtering unit 138c performs a function of determining whether the same lesion information is detected among the selected representative images, and when determining that the same lesion information is detected, handling the selected representative images as a duplicate image, and filtering the remaining representative images other than one of the selected representative images.

More preferably, the duplicate image filtering unit 138c obtains a probability of detecting the same lesion information among the selected representative images through the image processing program, and compares an inter-vector similarity of vectors acquired in a pre-coupling layer which is a last layer in the EfficientNetB6 structure of the image processing program through an Ann (approximate nearest neighbor)oy algorithm (approximate neighbor method), and determine whether the same lesion information is detected.

The notification module 140 performs a function of visually displaying according to the notification signal output from the control module 130 on an arbitrary screen.

The notification module 140 may be configured to include at least one of a liquid crystal display (LCD), a thin film transistor-liquid crystal display (TFT LCD), an organic light-emitting diode (OLED), a flexible display, and a 3D display.

Meanwhile, a method for controlling the system that assists an endoscopy diagnosis configured as such may be configured to include an endoscopic image providing step S100, a frame image conversion step S200, a lesion information detection step S300, a continuous detection recognition step (reference numeral not displayed), a diagnosis information generation step S500, a notification module display step S600, and a search region confirmation step S300'.

In the endoscopic image providing step S100, the endoscope module 110 provides an endoscopic image for body's internal organs of an arbitrary procedure target patient in real time.

In the frame image conversion step S200, the control module 130 acquires the endoscope image provided in the endoscopic image providing step S100 at a plurality of frames per second, and converts the frame image according to the acquisition to meet the condition of the image processing program.

In the lesion information detection step S300, the control module 130 analyzes the frame image converted in the frame image conversion step S200 through the image processing program to detect lesion information.

In the continuous detection recognition step, the control module 130 recognizes whether the lesion information is continuously detected in the frame images of 10 or more frames among the frame images converted in the frame image conversion step S200 according to a detection result S410 of the lesion information detection step S300 (S420).

In the continuous detection recognition step, the control module 130 allows the endoscopic image providing step S100 to be first performed again when the lesion information is not detected according to the detection result of the lesion information detection step S300.

In the diagnosis information generation step S500, the control module 130 matches the continuously detected lesion information and the medical information input from the input module 120 with each other through a lesion diagnosis program, and generates diagnosis information corresponding to the matching result when it is recognized that the lesion information is continuously detected in the frame images of 10 or more frames according to a recognition result of the continuous detection recognition step.

Here, in the diagnosis information generation step S500, the control module 130 allows the endoscopic image providing step S100 to be first performed again when it is recognized that the lesion information is not continuously detected in the frame images of 10 or more frames according to the recognition result of the continuous detection recognition step.

In addition, the diagnostic information generation step S500 may further include an image selection step S510 of selecting, when the control module 130 recognizes that the lesion information is continuously detected in the frame images of 10 or more frames according to the recognition result of the continuous detection recognition step, one representative frame image among the frame images of 10 or more frames through the image processing program.

As illustrated in FIG. 5, the image selection step S510 may be configured to include a blur image removal step S511, a representative image selection step S512, and a duplicate image filtering step S513.

In the blur image removal step S511, the control module 130 removes at least one blur image in which a blur phenomenon appears from the frame images of 10 or more frames.

In the representative image selection step S512, the control module 130 selects a plurality of representative images from the image list from which the blur image is removed through the blur image removal step S511.

In the duplicate image filtering step S513, the control module 130 determines whether the same lesion information is detected among the representative images selected in the representative image selection step S512, and when determining that the same lesion information is detected, handling the selected representative images as a duplicate image, and filters the remaining representative images other than one of the selected representative images.

In the notification module display step S600, the control module 130 outputs a preset notification signal according to the continuously detected lesion information and the diagnosis information generated in the diagnosis information generation step S500, and the notification module 140 visually displays on an arbitrary screen according to the notification signal output from the control module 130.

In the search region confirmation step S300', the control module 130 matches and classifies the frame images converted in the frame image conversion step S200 with respective regions of the internal organs of the body, respectively, and further generates search information for distinguishing a search completion region and an unsearched region according to the classification result, and outputs a preset notification signal according to the generated search information, and then performs a display process of the notification module 140 in the notification module display step S600.

Here, more specifically, as illustrated in FIG. 4, the search region confirmation step S300' may be configured to include a category-specific classification step S310', a continuous classification determination step S320', a search information generation step (reference numeral not displayed), and a notification signal output step S340'.

In the category-specific classification step S310', the control module 130 receives the frame image converted in the frame image conversion step S200 in real time and classifies which region of the internal organs of the body the frame image matches into an arbitrary category through the image processing program.

In the continuous classification determination step S320', the control module 130 determines whether the frame images classified in the category-specific classification step S310' are classified into the category of the same region continuously in 30 frames (S321'), and determines whether an endoscopic procedure is terminated according to a power signal of the endoscope module 110 (S322').

In the search information generation step, the control module 130 generates search information for distinguishing a search completion region and an unsearched region according to the determination result in the continuous classification determination step S320'.

In the search information generation step, when the control module 130 determines that the image frame is classified into the category of the same region continuously in 30 frames according to the determination result in the continuous classification determination step S320', the control module 130 handles the corresponding region as the search completion region in which the search by the endoscope module 110 is sufficient to generate first search information corresponding thereto (S331'), and when determining that the image frame is not classified into the category of the same region continuously in 30 frames at a time when the procedure using the endoscope module 110 is terminated, the control module 130 handles the corresponding region as the unsearched region in which the search by the endoscope module 110 is insufficient to generate second search information corresponding thereto.

In addition, in the search information generation step, when it is determined that the image frame is not classified into the category of the same region continuously in 30 frames at a time when the procedure using the endoscope module 110 is in progress, the endoscopic image providing step S100 is first performed again.

In the notification signal output step S340', the control module 130 outputs a preset notification signal according to the search information generated in the search information generation step, and then the display process of the notification module 140 in the notification module display step S600 is performed.

Detailed descriptions of the preferred exemplary embodiments of the present invention disclosed as described above are provided so as for those skilled in the art to implement and execute the present invention. The present invention has been described with reference to the preferred exemplary embodiments, but those skilled in the art will understand that the present invention can be variously modified and changed without departing from the scope of the present invention. For example, those skilled in the art may use the respective components disclosed in the exemplary embodiments by combining the respective components with each other. Therefore, the present invention is not limited to the exemplary embodiments described herein, but intends to grant the widest range which is coherent with the principles and new features disclosed herein.

The present invention may be embodied in other specific forms without departing from the spirit and essential characteristics of the present invention. Accordingly, the aforementioned detailed description should not be construed as restrictive in all terms and should be exemplarily considered. The scope of the present invention should be determined by rational construing of the appended claims and all modifications within an equivalent scope of the present invention are included in the scope of the present invention. The present invention is not limited to the exemplary embodiments described herein, but intends to grant the widest range which is coherent with the principles and new features presented herein. Further, the claims that are not expressly cited in the claims are combined to form an exemplary embodiment or be included in a new claim by an amendment after the application.

The invention claimed is:

1. A method for controlling a system that assists an endoscopy diagnosis based on artificial intelligence, the method comprising:

providing an endoscopic image for internal organs of a patient;

receiving medical information of the patient;

analyzing, using an image processing program, the endoscopic image to detect lesion information including a size, a shape, and coordinates of at least one lesion, matching the detected lesion information and the medical information, generating, using a lesion diagnosis program, at least one diagnosis information of malignancy and a malignancy probability corresponding to a result of the matching, and outputting a notification signal according to the detected lesion information and the at least one diagnosis information; and displaying the at least one diagnosis information on a screen according to the notification signal, wherein the endoscopic image is matched and classified with respective regions of the internal organs of patient, respectively, using the image processing program to which a deep learning model is applied, search information for distinguishing a search completion region and an unsearched region is generated based on the endoscopic image, and the notification signal is output according to the generated search information, wherein the deep learning model of the image processing program is pre-learned by first acquiring a plurality of frame images in which lesions appear in a plurality of endoscopic images acquired by pre-capturing internal organs of multiple patients, wherein the lesion diagnosis program is a deep learning-based program that is pre-matched and learned by first acquiring the plurality of frame images in which the lesions appear and a plurality of medical information of the multiple patients corresponding thereto, wherein the endoscopic image is acquired at a plurality of frames per second, wherein the plurality of frame images is converted to meet a condition of the image processing program, and wherein the plurality of frame images in which the lesions appear in the plurality of endoscopic images acquired by pre-capturing the internal organs of the multiple patients, the plurality of medical information for the multiple patients corresponding to the plurality of frame images in which the lesions appear, and a learning environment of the image processing program and a learning environment of the lesion diagnosis program are stored in a database.

2. The method of claim 1, wherein the image processing program is configured to acquire a lesion region on the endoscopic image by learning 10,000 to 11,000 frame images in which the lesions appear in the plurality of endoscopic images acquired by pre-capturing the internal organs of the multiple patients, acquire data for coordinates of the lesion region on the endoscopic image, and acquire data for a size and a shape of the lesion region on the endoscopic image through a pixel analysis.

3. The method of claim 1, wherein whether the lesion information is continuously detected in frame images of 10 or more frames among the plurality of frame images is recognized, and when the lesion information is continuously detected in the frame images of 10 or more frames, the frame images of 10 or more frames are separately stored.

4. The method of claim 1, wherein the lesion diagnosis program is configured to match and learn 2000 to 2100 frame images in which the lesions appear and 2000 to 2100 medical information of 2000 to 2100 patients corresponding thereto, diagnose a degree of malignancy for the lesions, and acquire data for the malignancy and a malignancy probability of the lesions.

5. The method of claim 1, wherein the plurality of frame images is classified into a total of 10 categories related to a gastrointestinal tract among the internal organs using the image processing program, and the 10 categories are esophagus, squamocolumnar junction, middle upper body, lower body, antrum, duodenal bulb, duodenal descending, angulus, retroflex middle upper body, and fundus.

6. The method of claim 1, wherein when the plurality of frame images is classified into a category of a same region continuously in 30 frames, a corresponding region is handled as the search completion region in which a search is sufficient to generate first search information corresponding thereto, and the notification signal which is displayed in a snapshot image or a text for the search completion region is output according to the first search information.

7. The method of claim 1, wherein the notification signal which is displayed in a snapshot image or a text for the unsearched region is output according to a second search information generated.

8. The method of claim 7, wherein the notification signal in the snapshot image is positioned to correspond to the coordinates of the at least one lesion in the lesion information, has a size corresponding to the size of the at least one lesion, and displays a polygonal solid line corresponding to the shape of the at least one lesion in a mapping form.

9. The method of claim 1, wherein the lesion information is continuously detected through the image processing program and one representative frame image is selected among frame images of 10 or more frames separately stored in the database, at least one blur image in which a blur phenomenon appears from the frame images of 10 or more frames separately stored in the database is removed using the image processing program, a plurality of representative images is selected from an image list from which the at least one blur image is removed, and whether a same lesion information is detected among the selected plurality of representative images is determined, and when the same lesion information is detected, the selected plurality of representative images is handled as a duplicate image, and remaining representative images other than the selected plurality of representative images are filtered.

10. The method of claim 9, wherein the image processing program learns the blur phenomenon based on 2700 to 2800 frame images in which the lesions appear in the plurality of endoscopic images acquired by pre-capturing the internal organs of the multiple patients.

11. The method of claim 9, wherein the image processing program learns detection of the same lesion information based on 6000 to 6100 frame images in which the lesions appear in the plurality of endoscopic images acquired by pre-capturing the internal organs of the multiple patients.

* * * * *